(12) United States Patent
Goodman et al.

(10) Patent No.: US 9,022,975 B2
(45) Date of Patent: May 5, 2015

(54) AIRLESS, NON-CLOGGING TIP ASSEMBLY AND DEVICE

(75) Inventors: John Goodman, Ann Arbor, MI (US);
Sonia Martins, Warren, NJ (US);
Joseph B. Bilotta, Bayonne, NJ (US)

(73) Assignee: Ethicon, Inc., Somerville, NJ (US)

( * ) Notice: Subject to any disclaimer, the term of this patent is extended or adjusted under 35 U.S.C. 154(b) by 286 days.

(21) Appl. No.: 13/611,511

(22) Filed: Sep. 12, 2012

(65) Prior Publication Data

US 2014/0074154 A1 Mar. 13, 2014

(51) Int. Cl.
| | | |
|---|---|---|
| *A61B 17/00* | (2006.01) | |
| *B01F 5/06* | (2006.01) | |
| *B01F 13/00* | (2006.01) | |
| *B05B 15/02* | (2006.01) | |
| *B05B 1/32* | (2006.01) | |

(52) U.S. Cl.
CPC ......... *A61B 17/00491* (2013.01); *B01F 5/0683* (2013.01); *B01F 5/069* (2013.01); *B01F 13/0023* (2013.01); *B05B 15/0291* (2013.01); *A61B 2017/00495* (2013.01); *B01F 2215/0039* (2013.01); *B05B 1/323* (2013.01)

(58) Field of Classification Search
CPC ............... A61B 17/00491; A61B 2017/00495; B05B 1/323; B05B 7/0408; B05B 11/04; B01F 5/0683; B01F 5/069
USPC ................ 606/213–217; 604/82, 89–91, 191; 222/137; 239/107
See application file for complete search history.

(56) References Cited

U.S. PATENT DOCUMENTS

| | | | | |
|---|---|---|---|---|
| 2,112,160 | A | * | 3/1938 | Johnson ........................ 604/518 |
| 3,395,344 | A | * | 7/1968 | Bader .......................... 324/71.1 |
| 5,116,315 | A | | 5/1992 | Capozzi et al. |
| 5,605,255 | A | | 2/1997 | Reidel et al. |
| 6,063,055 | A | | 5/2000 | Epstein et al. |
| 6,341,735 | B1 | | 1/2002 | Baudin |
| 6,884,232 | B1 | * | 4/2005 | Hagmann et al. ............... 604/82 |
| 8,408,480 | B2 | * | 4/2013 | Hull et al. ..................... 239/107 |
| 8,657,780 | B2 | * | 2/2014 | Palmer-Felgate ............... 604/91 |
| 2010/0096481 | A1 | | 4/2010 | Hull et al. |

FOREIGN PATENT DOCUMENTS

WO   2005/091720   10/2005

* cited by examiner

*Primary Examiner* — Kathleen Holwerda
(74) *Attorney, Agent, or Firm* — David R. Crichton

(57) ABSTRACT

The invention described herein is a device for dripping a tissue sealant and/or adhesive that comprises a) first and second barrels or syringes that contain first and second biocomponents that are disposed between proximal and distal ends; b) a plunger in each barrel and c) a drip tip comprising i) a support having distal and proximal ends and at least two fluid passageways from the distal to the proximal end that are in fluid communication with one of the barrels of the dispensing device on the proximal end; and ii) an endcap that fits over the support having at least two flexible hinges. The present invention is also directed to an assembly for mixing and drip dispensing two reactive biologic components as tissue sealant and/or hemostatic agent and to methods for delivering biologic components to achieve hemostasis and/or tissue sealant by drip dispensing from the device described above.

15 Claims, 3 Drawing Sheets

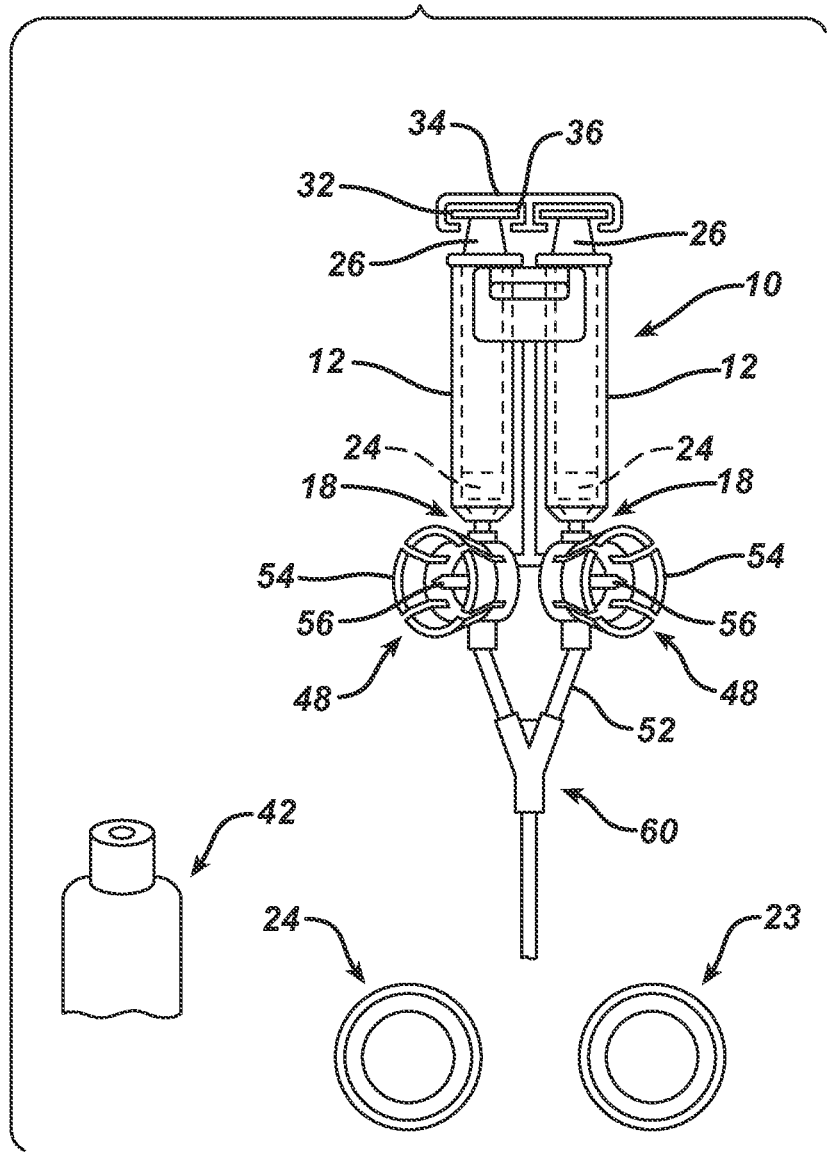

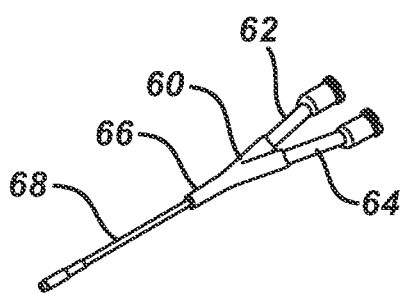
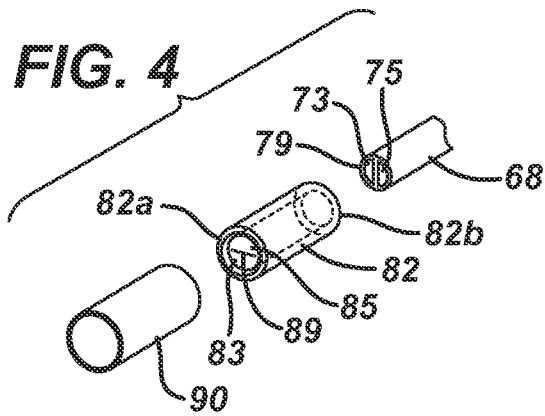
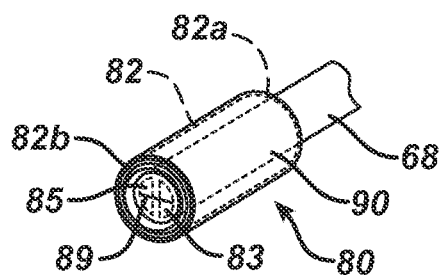
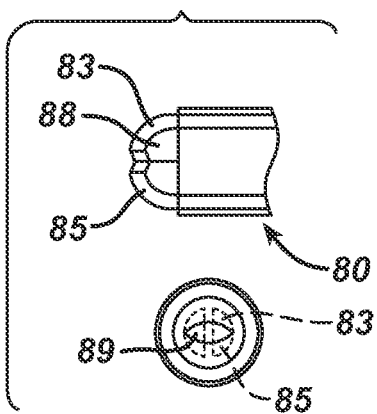
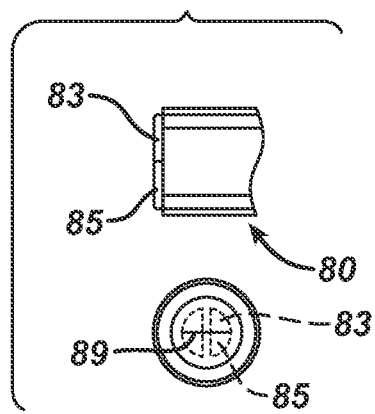

AIRLESS, NON-CLOGGING TIP ASSEMBLY AND DEVICE

The present disclosure relates to flexible drip tip assemblies for use with devices that mix and apply two or more biologic components. More particularly, the present disclosure relates to a drip tip assembly for use with a biologic drip device, wherein the drip tip is capable of self-clearing as a result of a flexible outlet design.

BACKGROUND

Drip devices for dispensing two or more biocomponents are known. In the medical device field, such devices are typically used for applying bioadhesives, polymers and other synthetic material used in wound closure. Because of the reactant nature of the biocomponents used to form the bioadhesive, mixing of the components does not occur until the solution is ready to be applied. Mixing of the components too soon before application may result in premature hardening of the mixture, thereby making application of the solution impossible. Thus, in known drip devices, the two or more components are maintained separately until just prior to application. The drip devices include one or more mixing means for mixing the two or more solutions prior to application. The mixing means may be passive, i.e., spiral configuration in the tubing, or instead may be active, i.e., mixing blade or impeller. Once mixed, the solution may be applied through a needle-like output or may instead be ejected through a spray assembly. Thorough mixing of the two or more components prior to application is important to ensure that the solution will perform as intended.

An exemplary device is taught in U.S. Pat. No. 5,116,315, entitled "Biological Syringe System", which discloses a system for delivery two fluids in a mixed composition, comprising a manifold and a discharge assembly. The discharge assembly mixes fluids in a mixing space and then atomizes the mixed fluids in a spray delivered from the assembly. Similarly, the device shown in U.S. Pat. No. 5,605,255, entitled, "Apparatus for Spraying a mixture of Two Components', is an apparatus for spraying a liquid mixture having two syringes, a connecting piece, a premixing chamber, and a reduced volume section downstream from premixing chamber, and an exit aperture for spraying the mixture. The reduced volume section terminates in a homogenization region. U.S. Pat. No. 6,063,055, entitled "Turbulence Mixing Head for a Tissue Sealant Applicator and Spray Head for Same", illustrates a device in which the mixing is performed in a mixing head.

Intermittent use of a biologics spray device, as may be required during a procedure, tends to clog the outlet of the applicator tip. As a result, most applicator assemblies are provided with a number of replacement tips for when clogging of the tip occurs. Replacing clogged applicator tips interrupts the flow of a procedure, is time consuming and is an added expense. The device in published U.S. Patent Application 2010/0096481, "Self-Cleaning Spray Tip", is described as having the distal end of drip cap assembly with an outlet that changes its configuration—at rest and at a second condition (e.g. during expression). The distal end is described as comprised of a material that permits flexion and expansion. The first and second reactive components are introduced into swirl chambers before mixing and are atomized as ejected through the outlet in a cone-shaped spray

SUMMARY

The invention described herein is a device for dripping a tissue sealant and/or adhesive that comprises a) first and second barrels or syringes that contain first and second biocomponents that are disposed between proximal and distal ends; b) a plunger in each barrel and c) a drip tip comprising i) a support having distal and proximal ends and at least two fluid passageways from the distal to the proximal end that are in fluid communication with one of the barrels of the dispensing device on the proximal end; and ii) an endcap that fits over the support having at least two flexible hinges, each hinge having a portion of their interior surface resting on a top surface of the distal end of the dual lumen support and distal outlets for the fluid passageways, wherein a mix chamber and an outlet are formed by expansion only when the first and second biocomponents are under sufficient dispensing pressure.

The present invention is in one embodiment directed to a device for mixing and drip dispensing two reactive biologic components as tissue sealant and/or hemostatic agent with a syringe support having holding elements for at least two syringes and an associated handle; at least a pair of syringes each having an outlet and containing a reactive biologic component; a first piston and second piston within the first and second syringes, respectively; a support having two separate fluid channels in communication with the syringe outlets for the first and second syringes; and an endcap that is positioned at the outlet of the support having an open proximal end and a closed distal end with a flexible diaphragm. The flexible diaphragm in combination with the distal face of the dual lumen support define a first volume and a second volume and a dispensing passageway, wherein said first volume is substantially zero and said second volume is sufficient to allow the two reactive biologic components to mix just prior to and/or during dispensing. Further, the dispensing passageway is closed when the first volume is substantially zero. The first volume of the flexible diaphragm transitions to said second volume in response to a dispensing pressure from the reactive biologic components flowing through the two fluid channels and transitions back to said first volume in response to a reduction of pressure acting on the biologic components within the fluid channels. The distal end of the endcap can be substantially circular, while the flexible diaphragm can be at least two flexible flaps that are circumferentially affixed to the endcap. Preferably, at least a portion of an interior-facing edge from each flexible flap is not affixed to the circumference of the endcap. The dispensing passageway through the endcap is preferably a linear gap as the flexible diaphragm expands distally in response to pressure from the lumens to dispense the components from the mixing volume.

In one embodiment, a polymeric layer or silicone oil is applied over at least one surface of the flexible diaphragm. The polymeric layer can contain a poly-para-xylylene material and/or derivatives thereof.

In another embodiment, the first syringe contains thrombin and the second syringe contains fibrinogen. Hence, the present invention is also directed to a method for delivering biologic components to achieve hemostasis and/or tissue sealant by drip dispensing from the device described above. The biologic components are preferably delivered in a surgical setting.

In another embodiment, the present invention is directed to an assembly for mixing and drip dispensing two reactive biologic components as tissue sealant and/or hemostatic agent having an endcap having a proximal end and distal end, wherein the proximal end is open and the distal end has a flexible diaphragm covering outlet of fluid passages, said flexible diaphragm in combination with the distal face of fluid passage outlets, defining a first volume and a second volume and a dispensing passageway, wherein said first volume is substantially zero and said second volume is sufficient to allow the two reactive biologic components to mix just prior to and/or during dispensing; and a support having at least two fluid passages that is positioned in the distal end of the endcap. Further, the dispensing passageway is closed when the first volume is substantially zero, and said first volume transitions to said second volume in response to a dispensing pressure from the reactive biologic components flowing through the fluid passages and transitions back to said first volume in response to a reduction of pressure acting on the biologic components within the fluid passages. The distal end of the endcap can be substantially circular while the flexible diaphragm can be at least two flexible flaps that are circumferentially affixed to the endcap. Preferably, at least a portion of an interior-facing edge from each flexible flap is not affixed to the circumference of the endcap. In one embodiment, a polymeric layer or silicone oil is applied over at least one surface of the flexible diaphragm. The polymeric layer is preferably poly-para-xylylene polymeric material and/or derivatives thereof.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2 illustrates a biologics loading device.
FIG. 3 illustrates a manifold section of the inventive device.
FIG. 4 illustrates an exploded view of the inventive drip cap assembly.
FIG. 5 illustrates an assembled drip cap assembly.
FIG. 6 illustrates the drip cap assembly under pressure.
FIG. 7 illustrates the drip cap assembly without pressure.

DETAILED DESCRIPTION

Figure 1:
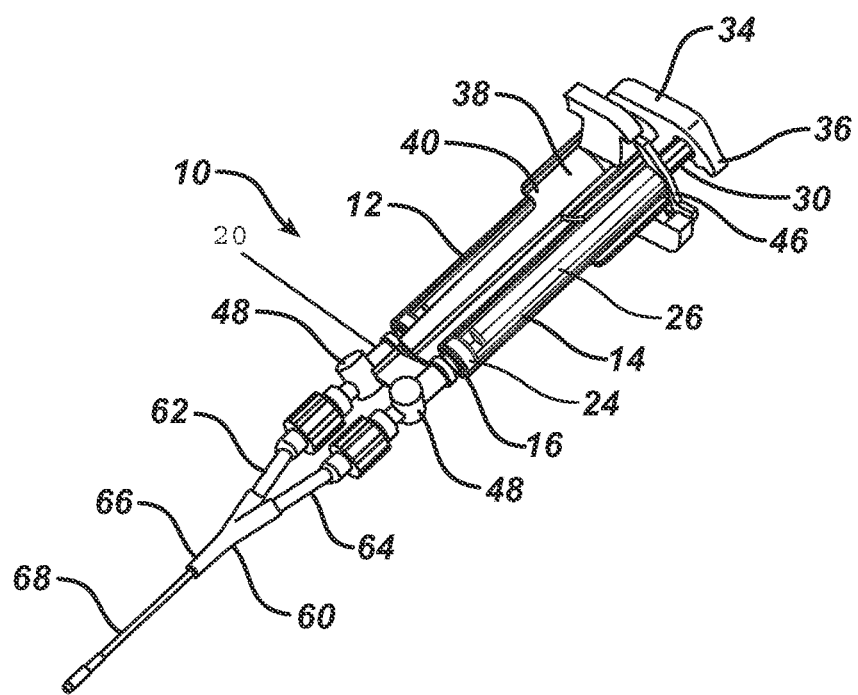
FIG. 1 illustrates the inventive device.

Referring initially to FIGS. 1 and 2, a spray device including a spray tip according the present invention is shown generally as spray device 10. Spray device 10 comprises two supply containers provided as commercially available syringes 12 for solutions of biologic agents, such as proteins, such as fibrinogen, and of fibrinolytic substances, such as thrombin, of a two-component tissue glue. Each syringe 12 comprises a hollow cylindrical syringe body 14 having a front end 16 with an outlet opening 18 and connecting pieces 20, and an open rear end 22 (not shown). Arranged in each syringe body 14 is a piston or plunger 24 in sealing abutment on the inner surface of syringe body 14. Piston 24 is held by a piston rod 26 guided out of syringe body 14 through the rear end 22. The piston rods 26 extend respectively in the longitudinal direction of the syringe bodies 14 and beyond open rear end 22. The free ends 30 of piston rods 26 facing away from piston 24 have annular flanges 32 formed thereon. These annular flanges 32 are mechanically connected to each other by a connecting element 34. Connecting element 34 is formed with two receiving recesses 36 which are laterally open and suited for insertion of the annular flanges 32 thereinto. The two syringe bodies 14 are connected to each other by a clip holding means 38 (hereinbelow referred to as a holding element).

The syringe bodies 14 are supported for sliding displacement on the holding element 38, because the resilient elastic holding clamps 40 extend by more than 180° and preferably by up to 200° around the syringe bodies 14 and thus enclose the syringe bodies 14 with a clamping force allowing for a relative displacement. The holding element 38 is arranged to bear on laterally protruding flanges 46 on the rear ends 22 of the syringe bodies 14, thus providing for a mutual abutment of holding element 38 and syringe body 14.

As evident from FIG. 2, the slightly conical connecting pieces 20 on the front ends 16 of the syringe bodies 14 are respectively connected to a fluid control device 48. Each fluid control device 48 is provided with a connector for receiving the conical connecting piece 20 of a syringe both 14. Each fluid control device 48 is provided with an outlet connecting piece 52 opposite to a connector. Further, each fluid control device 48 is provided with a receiving adaptor 54 comprising a fluid conduit member 56. The receiving adaptor 54 is configured for insertion of a medicinal vessel thereinto, with the fluid conduit member, formed as a puncturing needle, penetrating the rubber closure plug of a vessel 42 and extending into the interior of the vessel 42. Each fluid control device 48 has a floor control member rotatably supported therein. This flow control member can be rotated from outside, which is performed particularly by rotating the adaptor 54. By rotating the flow control member, the flow control member can be moved from a first fluid control position wherein a fluid path exists between a syringe body 14 and the medicinal vessel, into a second fluid control position wherein the syringe body 14 is in fluid connection with the outlet connecting piece 52 of fluid control device 48. In an alternative embodiment, a spray device 10 can use pre-filled syringes so that the fluid control devices are not required to enable filling and subsequent use.

With reference now to FIG. 3, manifold 60 includes a substantially Y-shaped member having a first and a second proximal extension 62, 64 and a distal extension 66. Proximal extensions 62, 64 are configured for operable engagement with a first and a second source of component (not shown), e.g., syringes. Distal extension 66 is configured for operable engagement with elongated shaft 68, as will be discussed in further detail below. Manifold 60 further includes first and second component channels (not shown). First and second component channels fluidly communicate the first and second sources of components with a first and a second lumen 73, 75 formed in elongated shaft 68 as shown in FIG. 4. While manifold 60, as shown, is configured to receive only two sources of component, it is envisioned that manifold 60 may be configured to receive more than two sources of biological/medicinal components.

Referring back to FIG. 3, elongated shaft 68 may define a substantially solid body of silicone, plastic, polymer or other flexible material. As noted above, elongated shaft 68 includes first and second component lumens 73, 75 extending the length thereof. A wire (not shown) composed of a malleable material can also extend the length of elongated shaft 68. Wire 76 can maintain elongated shaft 68 in a bent or flexed configuration after elongated shaft 68 has been bent or flexed to accommodate a given procedure. Elongated shaft 68 is secured to distal extension 66 of manifold 60 such that first and second component lumens 73, 75 align with first and second component channels. Alternatively, elongated shaft 68 may be integrally formed at a distal end of manifold 60.

With reference now to FIGS. 4 and 5, drip cap assembly 80 defines a substantially cylindrical body 82 having an open proximal end 82b and a substantially closed distal end 82a Open proximal end 82b is configured to receive distal end of elongated shaft 68 as shown in FIG. 5. Cylindrical body 82 is affixed to elongated shaft 68, preferably by heat sealing. Cylindrical body 82 can be removable or permanently attached. Alternative means for securing cylindrical body 82, such as via a twist or screw-on configuration or a snap-fit over a detent ring can also be used. As will be discussed in further detail below, distal end 82b includes a slit outlet 89 that is configured to eject a thoroughly mixed solution. Slit outlet 89 has at least two flexible flaps 83, 85 that, in the absence of pressure, rest immediately against outlets for component lumens 73, 75 through elongated shaft 68. Slit outlet 89 preferably is a central dividing line between the outlets for first and second component lumens 73, 75. In an alternative embodiment (not illustrated), slit outlet 89 can be moved from a central location to be positioned relatively upward or down from the central axis line both bisecting lumen 73, 75. In a still further embodiment (also not illustrated), slit outlet 89 can be rotated so as to be oriented along a line that divides lumen 73, 75 or at an angle thereto. An optional cap 90 having a cylindrical shape with two open ends can be provided that slides over and fits along the exterior surface of drip cap assembly 80.

Referring to FIGS. 5, 6, and 7, drip cap assembly 80 has two operational states depending on whether or not the two biocomponents are under sufficient dispensing pressure. The first operational state exists when the two components are not under sufficient dispensing pressure as shown in FIGS. 5 and 7. In this state, the interior surfaces of flaps 83, 85 of drip cap assembly 80 rest in direct contact with surface 79 and the outlets for first and second lumens 73, 75. The second operational state exists when the two components are under pressure as result of operator acting on connecting element 34 that transmits force through piston rods 26 and plungers 24. The pressure exerted by the liquid components creates a mixing volume 88 and outlet 89 as shown in FIG. 6 between drip cap assembly 80 and the outlets for first and second lumens 73, 75.

Mixing volume 88 is created as a result of pressure from the incoming biologic components flowing through first and second lumens 73, 75 that flexes and expands flaps 83, 85, while it holds the remainder of drip cap assembly 80 stays in place. Mixing volume 88 will exist for so long as sufficient pressure is applied against drip cap assembly 80. In the absence of sufficient pressure from the liquid components, drip cap assembly returns to the first operational state in which there is no liquid component mixing in mixing volume 88.

Mixing volume 88, when present, defines a substantially curved conical volume having a flat proximal surface formed by the outlets from first and second lumens 73, 75. The shape and volume mixing volume 88 must be sufficient to allow mixing of the two liquid components. Additionally, in order to ensure drip cap assembly 80 and flaps 83, 85 retain sufficient flexibility and functionality, it has been found that a coating of Parylene, silicone oil or similar materials should be applied. Parylene is the generic name for members of a specific polymer series. The basic members of the series, called Parylene N, is poly-para-xylylene, a completely linear, highly crystalline material. Parylene C is produced from the same monomer modified only by the substitution of a chlorine atom for one of the aromatic hydrogens. Parylene D is produced from the same monomer modified by the substitution of the chlorine atom for two of the aromatic hydrogens. Parylene coatings are applied by vacuum deposition. The Parylene series of polymers are known in the art and commercially available. Additionally, it has been found desirable to ensure complete curing of the flexible diaphragm prior to placement of the slit so that subsequent sterilization activities do not induce further curing or crosslinking reactions that can cause the slit to reseal.

The operation of spray device 10 will now be described as relates to the figures. Prior to use, drip cap assembly 80 is affixed to the distal end of elongated shaft 68. First and second holders (23, 24) with vessels 42 for sources of first and second component are next connected to first and second fluid control devices 48 and drawn into syringes 12. Once secured to manifold 60, first and second components may be activated by depression of syringe plungers (not shown), to initiate the flow of first and second components within first and second component channels 63, 65, respectively. The first and second components flow through first and second component channels 62, 64, through first and second component lumen 73, 75, respectively, and into drip cap assembly 80. The first and second components flowing from first and second component lumens 73, 75 enter mixing volume 88 where they are mix and are directed out through flaps 83, 85 and outlet 89.

During operation of drip cap assembly 80, momentary stoppages in the application of pressure for a period of time could result in the formation of a clog or obstruction that may obstruct outlet 89. However, as pressure is released, drip cap assembly 80 returns to its first operational state in which flaps 83, 83 rest directly against the outlets for first and second lumens 73, 75 to eliminate any clog or obstruction.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

We claim:

1. A device for mixing and drip dispensing two reactive biologic components as tissue sealant and/or hemostatic agent comprising:
   a) a syringe support having holding elements for at least two syringes and an associated handle;
   b) at least a pair of syringes each having an outlet and containing a reactive biologic component;
   c) a first piston and second piston within the first and second syringes, respectively;
   d) a support having two separate fluid channels in communication with the syringe outlets for the first and second syringes, each of the fluid channels having a fluid channel outlet; and
   e) an endcap positioned at a distal outlet of the support having an open proximal end and a closed distal end with a flexible diaphragm having at least a slit outlet having at least two flexible flaps that, in the absence of pressure, rest against the fluid channel outlets, said flexible diaphragm in combination with a distal face of the support, defining a first volume and a second volume and a dispensing passageway, wherein said first volume is substantially zero and said second volume is sufficient to allow the two reactive biologic components to mix just prior to and/or during dispensing and further wherein said dispensing passageway is closed when the first volume is substantially zero, and said first volume transitions to said second volume in response to a dispensing pressure from the reactive biologic components flowing through the two fluid channels and transitions back to said first volume in response to a reduction of pressure acting on the biologic components within the fluid channels.

2. A device according to claim 1 wherein the distal end of the endcap is substantially circular and the at least two flexible flaps comprise at least two elastically, deformable sections that are circumferentially affixed to the endcap.

3. A device according to claim 2 wherein at least a portion of an interior-facing edge from each elastically, deformable section is not affixed to the circumference of the endcap.

4. A device according to claim 3 wherein the dispensing passageway through the endcap is a contoured gap as the flexible diaphragm expands distally in response to pressure from the fluid channels to dispense the components from the second volume.

5. A device according to claim 1 wherein a polymeric layer or silicone oil is applied over at least one surface of the flexible diaphragm.

6. A device according to claim 5 wherein the polymeric layer comprises poly-para-xylylene or derivatives thereof.

7. A device according to claim 1 wherein a clip element connects and coordinates downward movement of plungers affixed to the first and second pistons.

8. A device according to claim 1 wherein the first syringe contains thrombin and the second syringe contains fibrinogen.

9. A method for delivering biologic components to achieve hemostasis and/or tissue sealing, the method comprising drip dispensing the biologic components from the device according to claim 1.

10. A method according to claim 9 wherein the biologic components are delivered in a surgical setting.

11. An assembly for mixing and drip dispensing two reactive biologic components as tissue sealant and/or hemostatic agent comprising:
   a) a support having at least two fluid passages, the support being positioned in a distal end of an endcap;
   b) the endcap having a proximal end and the distal end, wherein the proximal end is open and the distal end has a flexible diaphragm having at least a slit outlet defined by at least two flexible flaps that, in the absence of pressure, rest against outlets for the fluid passages, said flexible diaphragm in combination with a distal face of the fluid passage outlets, defining a first volume and a second volume and a dispensing passageway, wherein said first volume is substantially zero and said second volume is sufficient to allow the two reactive biologic components to mix just prior to and/or during dispensing and further wherein said dispensing passageway is closed when the first volume is substantially zero, and said first volume transitions to said second volume in response to a dispensing pressure from the reactive biologic components flowing through the fluid passages and transitions back to said first volume in response to a reduction of pressure acting on the biologic components within the fluid passages.

12. An assembly according to claim 11 wherein the distal end of the endcap is substantially circular and the at least two flexible flaps comprise at least two elastically, deformable sections that are circumferentially affixed to the endcap.

13. An assembly according to claim 12 wherein at least a portion of an interior-facing edge from each flexible flap is not affixed to the circumference of the endcap.

14. An assembly according to claim 11 wherein a polymeric layer or silicone oil is applied over at least one surface of the flexible diaphragm.

15. An assembly according to claim 14 wherein the polymeric layer comprises poly-para-xylylene or derivatives thereof.

* * * * *